United States Patent [19]

Kohnert et al.

[11] Patent Number: 5,352,453
[45] Date of Patent: Oct. 4, 1994

[54] COMPOSITIONS CONTAINING NON-GLYCOSYLATED HUMAN TISSUE TYPE PLASMINOGEN ACTIVATOR

[75] Inventors: Ulrich Kohnert, Habach; Rainer Rudolph, Weilheim, both of Fed. Rep. of Germany

[73] Assignee: Boehringer Mannheim GmbH, Mannheim-Waldhof, Fed. Rep. of Germany

[21] Appl. No.: 741,483

[22] Filed: Aug. 6, 1991

[30] Foreign Application Priority Data

Dec. 20, 1989 [DE] Fed. Rep. of Germany ....... 3942143

[51] Int. Cl.$^5$ .................... A01K 37/48; A01K 37/62; A01K 37/547; C12N 9/96
[52] U.S. Cl. ................. 424/94.64; 424/94.1; 424/94.3; 435/188
[58] Field of Search ............ 424/94.64, 94.1, 94.3; 435/188

[56] References Cited

U.S. PATENT DOCUMENTS

| | | | |
|---|---|---|---|
| 4,505,893 | 3/1985 | Mori et al. | 424/94.64 |
| 4,568,544 | 2/1986 | Hasegawa et al. | 424/94.1 |
| 4,837,022 | 6/1989 | Kakimoto et al. | 424/94.64 |
| 4,980,165 | 12/1990 | Isaacs et al. | 424/94.64 |
| 4,985,245 | 1/1991 | Kakimoto et al. | 424/94.3 |
| 5,068,106 | 11/1991 | Pâques et al. | 424/94.64 |
| 5,149,540 | 9/1992 | Kunihiro et al. | 424/94.3 |

FOREIGN PATENT DOCUMENTS

| | | |
|---|---|---|
| 0211592 | 2/1987 | European Pat. Off. . |
| 0228862 | 7/1987 | European Pat. Off. . |
| 0297294 | 1/1989 | European Pat. Off. . |
| 9108765 | 6/1991 | PCT Int'l Appl. . |

OTHER PUBLICATIONS

Larsen, G. R., et al., "Blood," vol. 73(7), Mar. 15, 1989, pp. 1842–1850.
Martin. U., et al., "Thrombosis Research," vol. 62(3), 1991, pp. 137–146.
Celley, R. F.; et al., "Biochemistry," vol. 8, 1989, pp. 4047–4054.

*Primary Examiner*—Douglas W. Robinson
*Assistant Examiner*—Kristin K. Larson
*Attorney, Agent, or Firm*—Felfe & Lynch

[57] ABSTRACT

Pharmaceutical compositions containing non-glycosylated human tissue type plasminogen activator (t-PA) having enzymatic activity of at least 0.1 MU/ml are disclosed. The compositions have a pH of from 4.5 to 6, contain citrate, and at least one other compound.

25 Claims, No Drawings

COMPOSITIONS CONTAINING NON-GLYCOSYLATED HUMAN TISSUE TYPE PLASMINOGEN ACTIVATOR

The human tissue plasminogen activator (t-PA) possesses great therapeutic importance for the dissolving blood coagula, e.g. in the case of heart infarcts. t-PA brings about the dissolution of blood coagula by the activation of plasminogen to plasmin. Plasmin in turn dissolves fibrin, the main component of the protein matrix of coagulated blood.

Natural t-PA is composed of several functional domains F, E, K1, K2 and P. The domain P contains the proteolytically active center which brings about the cleavage of plasminogen to plasmin. Gene technological production of t-PA or of various t-PA mutants, in which one or more of the domains F, E, K1 and K2 are deleted, in eukaryotic and prokaryotic cells, is already known. In contrast to natural t-PA, t-PA derivatives are synthesized from prokaryores in non-glycosylated form.

Furthermore, it is known that the sugar part has considerable influence on the solubility and aggregation of proteins (J. Biol. Chem. 263 (1988), 8832–8837). It has now been found that non-glycosylated t-PA is substantially less soluble than glycosylated t-PA.

Non-glycosylated t-PA (t-PA pro) dissolves very poorly in buffers usually employed for the solubilization of proteins, such as 50 mmol/l. Na titrate, 50 mmol/l. phosphate or physiological NaCl solution. However, for use as a therapeutically active material, t-PA pro should be present with a comparatively high enzymatic activity of at least 0.1 MU/ml., preferably of 0.1 MU/ml. to 10 MU/ml. The activity is defined according to WHO i.e., the World Health Organization, National Institute for Biological Standards and Control (ZGIMAL 42 (1987), 478–486).

From EP-S 0,217,379, it is known to increase the solubility of t-PA from prokaryotes by using neutral or slightly alkaline arginine formulations. However, a disadvantage of this process is that good solubilities of t-PA pro can only De achieved with very high arginine concentrations.

Consequently, it is the aim of the invention to develop pharmaceutical preparations which contain t-PA pro with an activity of more than 0.1 MU/ml., whereby t-PA pro is stable over a comparatively long period of time.

This is achieved by preparing a pharmaceutical composition of a non-glycosylated t-PA with an enzymatic activity of at least 0.1 MU/ml. with a pH of 4.5 to 6, which contains Citrate and at least one compound selected from the group consisting of
a) ascorbic acid,
b) EDTA,
c) an amino compound of the formula

whereby X=$SO_3H$, $CH(NH_2)$-$CO_2H$, $CO_2H$, H, $NH_2$ or OH, R=$C_1$-$C_9$-alkylene, $C_3$—$C_6$-cycloalkylene or benzylidene and $R^1$ is H or $C_1$-$C_3$ alkyl and $R^2$, is H or $C_1$-$C_3$-alkyl,
d) guanidinobutyric acid,
e) dimethylbiguanide,
f) arginine,
g) glucosamine,
h) fructose,
i) a pyrimidine nucleoside,
j) a pyrimidine nucleotide, and
k) a carboxylic acid substituted with one or more.

By t-PA pro, according to the present invention, one understands a t-PA which begins with an amino acid from −3 (Gly) to +1 (Ser) and ends at 527 (Pro) (nomenclature according to Harris, Protein Engineering, Volume 1 (1987) 449–458) as shown in FIG. 1. A t-PA pro is obtainable, e.g., according to the process described in WO 87/02673.

A citrate buffer is especially suitable for the solubilization of t-PA pro. The concentration of the citrate ions is at least 5 mmol/l., preferably of 5 to 100 mmol/l. An preferred concentration one the of 50 mmol/l. Depending upon the alkalinity of the added compound, the pH value is preferably adjusted with HCl or a base, such as e.g. NaOH or KOH.

Surprisingly, it was ascertained that the solubility of non-glycosylated t-PA in a buffer other than a citrate buffer system, e.g. phosphate buffer, is, in the case of equal ionic strength and equal pH value, substantially smaller. It has proven to be suitable to adjust the pH value of alkaline citrate solutions with HCl, i.e. so that the composition additionally contains chloride ions. In the presence of chloride ions, surprisingly, highly concentrated solutions of t-PA pro are substantially more stable than they are e.g., in the presence of phosphate ions. The pH value of acidic citrate solutions is usually adjusted with NaOH.

Suitable for a composition according to the invention is a pH value between 4.5 and 6.5, a pH value of 6 being preferred.

For a composition according to the invention, preferred amino compounds taurine, 4-aminobutanol-1, 5-aminopentanol-1, 6-aminohexanol-1, 1,9-diaminononane, 1,8-diaminooctane, 1,7-diaminoheptane, 1,6-diaminohexane, 1,5-diaminopentane, 1,4-aminobutane, 1, 3-aminopropane, lysine, ornithine, 8-aminooctanoic acid, 7-aminoheptanoic acid, ε-aminocaproic acid, δ-aminovaleric acid, γ-aminobutyric acid, tranexamic acid or p-aminomethylbenzoic acid. The preferred concentration for taurine and analogous compounds amounts to 0.1 to 0.5 mol/1., a concentration of 0.1 to 0.3 mol/1 being preferred . 4-Aminobutanol-1, 5-aminopentanol-1, 6-aminohexanol-], 1,9-diaminononane, 1,8-diaminooctane, 1,7-diaminoheptane, 1,6-diaminohexane, 1,5-diaminopentane, 1,4-diaminobutane or 1,3-diaminopropane are preferably used at concentrations of 10 to 100 mmol/l. Lysine, ornithine, 8-aminooctanoic acid , 7-aminoheptanoic acid, ε-aminocaproic acid, δ-aminovaleric acid, γ-aminobutyric acid, tranexamic acid or p-aminomethylbenzoic acid are preferably used at concentrations of 0.5 to 20 mol/l., concentrations of 1 to 10 mmol/l being preferred.

As a substituted carboxylic acid i.e., one substituted with one or more hydroxyl, keto and/or further carboxyl groups, one uses e.g. malic acid, lactic acid, fumaric acid or oxoglutaric acid. These substances are preferably used at concentrations from 1 mmol/l. to ]000 mmol/l., with 10 to 500 mmol/l being preferred.

Guanidinobutyric acid or arginine are preferably used at concentrations of from 10 to 200 mmol/l., with 50 to 100 mmol/l being preferred. For dimethylbiguanide, the concentration amounts to 50 to 400 mmol/l., preferably to 100 to 300 mmol/l.

EDTA is preferably used at concentration of from 1 to 100 mmol/l., with 10 to 100 mmol/l being. Ascorbic acid is preferably used at a concentration of from 0.1 to 1 mol/l., especially preferred being a concentration of from 0.2 to 0.3 mol/l.

Glucosamine and fructose are preferably used in concentrations of 1 to 500 mmol/l., especially preferred being concentrations of from 10 to 300 mmol/l.

As pyrimidine nucleosides and pyrimidine nucleotides thymidine, cytosine and uridine and the corresponding nucleotides are suitable. They are preferably used in concentrations of 1 to 300 mmol/l., especially preferred being those of from 10 to 300 mmol/l.

Furthermore, a subject of the invention is a composition according to the invention which additionally contains one or more amino acids, especially histidine.

In the following is set out a series of especially preferred preparations according to the present invention is set forth.

One formulation contains 50 mmol/l, Na citrate/NaOH, and 0.1 to 0.3 mol/l taurine, said formulation having a pH of 6.0. Also preferred is a formulation containing 50 mmol/l, Na citrate/HCl, and 0.2 to 0.3 mmol/l ascorbic acid, having a pH of 6.0.

A preferred formulation with 50 mmol/l. Na citrate/HCl, pH 6, and 1 mmol/l. to 10 mmol/l. 7-aminoheptanoic acid, 8-aminooctanoic acid, p-aminomethylbenzoic acid, ε-aminocaproic acid, δ-aminovaleric acid, γ-aminobutyric acid, tranexamic acid or ornithine.

Especially preferred are formulations which contain 50 mmol/l. Na citrate/HCl, pH 6.0, and 50 to 100 mmol/l. guanidinobutyric acid or arginine.

Also preferred is a formulation which contains 50 mmol/l. Na citrate, pH 6, and 10 to 100 mmol/l. EDTA. another preferred, formulation contains 50 mmol/l. Na citrate/HCl, and 100 to 300 mmol/l. dimethylbiguanide. biguanide, the formulation having a pH of 6.

An additional formulation contains 50 mmol/l. Na citrate/HCl, and 10 to 300 mmol/l. thymidine, cytosine or uridine, said formulation having a pH of 6. Yet another formulation contains 50 mmol/l. Na citrate/HCl, and 10 to 100 mmol/l. 4-aminobutanol-1, 5-aminopentanol-1, 6-aminohexanol-1, 1,9-diaminononane, 1,8-diaminooctane, 1,7-diaminoheptane, 1,6-diaminohexane, 1,5-diaminopentane, 1,4-diaminobutane or 1,3-diaminopropane, said formulation having a pH of 6. Still another formulation contains 50 mmol/l. Na citrate/HCl, and 10 to 300 mmol/l. fructose or glucosamine, said formulation having a pH of 6.

A final formulation contains 50 mmol/l. Na citrate, pH 6, and 10 to 500 mmol/l. malic acid, lactic acid, fumaric acid or 2-oxoglutaric acid.

Combinations of all of the above-mentioned compounds with citrate bring about very good solubility of proteins with t-PA activity.

Finally, a subject of the invention is a medicament based on a protein with t-PA activity as active material in solution or as lyophilisate with the given active materials and possibly also further pharmaceutically compatible additive, adjuvant, carrier and filling materials.

The pharmaceutical compositions according to the invention are preferably used as injection or inffusion solutions, i.e., a solution already ready for injection is made available which possesses the composition according to the invention. However, it is also possible to make available the pharmaceutical preparations in the form of lyophilisates. These are then reconstituted with known agents or solutions suitable for injection purposes. As injection medium, water is preferably used which contains the additives usual in the case of injection solutions, such as stabilizing agents, solubilizing agents, buffers and isotonic additives, for example a physiological NaCl concentration. Such additives are, for example, mannitol, tartrate or citrate buffer, ethanol, complex formers, such as e.g. ethylenediamine-tetraacetic acid and its non-toxic salts, as well as high molecular weight polymers, such as liquid polyethylene oxide for viscosity regulation. Liquid carrier materials for injection solutions must be sterile and are preferably filled into ampoules.

Finally, the invention also comprises the use of t-PA pro for the production of pharmaceutical preparations according to the invention.

The following Examples explain the invention.

EXAMPLE 1

Solubility of t-PA pro

Purified t-PA pro (dissolved in 0.5 tool/1 . arginine/H$_3$PO$_4$, pH 7.2) is concentrated by ultrafiltration over a YM 10 membrane (AMICON). In each case, 1 ml. of the concentrate (activity: 2.4 MU/ml.) is dialyzed against the buffers set out in Table 1. After centrifugation of the sample, the enzymatic activity is measured in the clear supernatant.

The measurement of the tPA activity can be determined in the usual way by cleavage of a chromogenic substrate (H. Lill, ZGIMAL 42 (1987), 478–486). The unit U is a unit of activity according to the definition of the WHO, National Institute for Biological Standards and Control.

TABLE 1

| buffer | activity MU/ml. | MU |
|---|---|---|
| 50 mmol/l. Na citrate/NaOH, pH 6 0.3 mol/l. taurine | 0.34 | 0.20 |
| 50 mmol/l. Na citrate/HCl, pH 6 0.3 mol/l. fructose | 0.12 | 0.07 |
| 50 mmol/l. Na citrate/NaOH, pH 6 0.3 mol/l. ascorbic acid | 0.34 | 0.18 |
| 50 mmol/l. Na citrate/HCl, pH 6 10 mmol/l. ε-aminocaproic acid | 0.21 | 0.28 |
| 50 mmol/l. Na citrate/HCl, pH 6 10 mmol/l. lysine | 0.17 | 0.12 |
| 50 mmol/l. Na citrate/HCl, pH 6 10 mmol/l. tranexamic acid | 0.26 | 0.36 |
| 50 mmol/l. Na citrate/HCl, pH 6 10 mmol/l. p-aminomethylbenzoic acid | 0.24 | 0.33 |
| 50 mmol/l. Na citrate/HCl, pH 6 0.3 mol/l. dimethylbiguanide | 1.20 | 1.50 |
| 0.05 mol/l. Tris/HCl, pH 7.2 | 0.01 | 0.01 |
| 50 mmol/l. NH$_4$HCO$_3$ | 0.05 | 0.40 |
| 50 mmol/l. Na citrate/HCl, pH 6 10 mmol/l. δ-aminovaleric acid | 0.17 | 0.23 |
| 50 mmol/l. Na citrate/HCl, pH 6 10 mmol/l. γ-aminobutyric acid | 0.27 | 0.20 |
| 50 mmol/l. Na citrate/HCl, pH 6 10 mmol/l. 7-aminoheptanoic acid | 0.20 | 0.27 |
| 50 mmol/l. Na citrate/HCl, pH 6 50 mmol/l. arginine | 0.19 | 0.21 |
| 50 mmol/l. Na citrate/HCl, pH 6 50 mmol/l. guanidinobutyric acid | 0.16 | 0.19 |
| 50 mmol/l. Na citrate/HCl, pH 6 10 mmol/l. EDTA | 0.10 | 0.12 |
| 50 mmol/l. Na citrate/NaOH, pH 6 50 mmol/l. EDTA | 0.18 | 0.22 |
| 50 mmol/l. Na citrate/NaOH, pH 6 100 mmol/l. ETDA | 0.26 | 0.29 |
| 50 mmol/l. Na citrate/HCl, pH 6 50 mmol/l. 1,6,-diaminohexane | 0.29 | 0.37 |
| 50 mmol/l. Na citrate/HCl, pH 6 50 mmol/l. 5-aminopentanol | 0.29 | 0.36 |
| 50 mmol/l. Na citrate/HCl, pH 6 | 0.27 | 0.28 |

TABLE 1-continued

| buffer | activity MU/ml | MU |
|---|---|---|
| 0.3 mol/l. glucosamine 50 mmol/l. Na citrate/HCl, pH 6 | 0.16 | 0.21 |
| 0.1 mol/l. thymidine 50 mmol/l. Na citrate/HCl, pH 6 | 0.07 | 0.09 |
| 50 mmol/l. Na₂HPO₄/H₂PO, pH 6 | 0.02 | 0.03 |
| 50 mmol/l. Na citrate/NaOH, pH 6 0.3 mol/l. fumaric acid | 0.19 | 0.19 |

We claim:

1. A composition having human tissue type plasminogen activator (t-PA) activity consisting essentially of a non-glycosylated t-PA pro having enzymatic activity of at least 0.1 MU/ml, a citrate and at least one compound selected from the group consisting of:
   (a) ascorbic acid;
   (b) EDTA;
   (c) an amino compound selected from the group consisting of taurine, 4-aminobutanol-1, 5-aminopentanol-1, 6-aminohexanol-1, 1,9-diaminononane, 1,8-diaminooctane, 1,7-diaminoheptane, 1,6-diaminohexane, 1,5-diaminopentane, 1,4-diaminobutane, 1,3-diaminopropane, lysine, ornithine, 8-aminooctanoic acid, 7-diaminoheptanoic acid, ε-aminocaproic acid, ε-aminovaleric acid, δ-aminobutyric acid, tranexamic acid and p-aminomethylbenzoic acid;
   (d) guanidinobytric acid;
   (e) dimethylbiguanide;
   (f) a pyrimidine nucleoside;
   (g) a pyrimidine nucleotide; and
   (h) a carboxylic acid substituted at least once with a hydroxyl group, keto group, or a carboxyl group wherein said composition has a pH of from 4.5 to 6.

2. The composition of claim 1, wherein said carboxylic acid is selected from the group consisting of malic acid, lactic acid, fumaric acid and 2-oxoglutaric acid.

3. The composition of claim 1, wherein said citrate is present at a concentration of from 5 to 100 mmol/l.

4. The composition of claim 3, wherein said citrate is present at a concentration of 50 mmol/l.

5. The composition of claim 1, further comprising a chloride ion.

6. The composition of claim 1, having 50 mmol/l Na citrate, 0.1 to 1 mol/1 of ascorbic acid and a pH of 6.

7. The composition of claim 6, wherein said ascorbic acid is present at a concentration of from 0.2 to 0.3 mol/1.

8. The composition of claim 1, having 50 mmol/l Na citrate, 1 to 200 mmol/l EDTA and a pH of 6.

9. The composition of claim 8, wherein said EDTA is present at a concentration of from 10 to 100 mmol/l.

10. The composition of claim 1 having 50 mmol/l Na citrate, 0.1 to 0.5 mol/1 taurine and a pH of 6.

11. The composition of claim 10, wherein said taurine is present at a concentration of from 0.1 to 0.3 mol/1.

12. The composition of claim 1 having 50 mmol/l Na citrate/HCl, 0.5 to 20 mmol/l of an amino compound selected from the group consisting of lysine, ornithine, 8-aminooctanoic acid, 7-aminoheptanoic acid, ε-aminocaproic acid, δ-aminovaleric acid, γ-aminobutyric acid, tranexamic acid and p-aminomethylbenzoic acid, and a pH of 6.

13. The composition of claim 1 having 50 mmol/l Na citrate/HCl, 10 to 100 mmol/l of an amino compound selected from the group consisting of 4-aminobutanol-1, 5-aminopentanol-1, 6-aminohexanol-1, 1,3-diaminopropane, 1,4-diaminobutane, 1,5-diaminopentane, 1,6-diaminohexane, 1,7-diaminoheptane, 1,8-diaminooctane and 1,9-diaminononane, and a pH of 6.

14. The composition of claim 1 having 50 mmol/l Na citrate/HCl, 10 to 200 mmol/l, of either guanidinobutyric acid or arginine and a pH of 6.

15. The composition of claim 14, wherein said guanidinobutyric acid or arginine is present at a concentration of from 50 to 100 mmol/l.

16. The composition of claim 1 having 50 mmol/l Na citrate/HCl, 50 to 400 mmol/l dimethylbiguanide, and a pH of 6.

17. The composition of claim 16, wherein said dimethylbiguanide is present at a concentration of from 100 to 300 mmol/l.

18. The composition of claim 1 having 50 mmol/l Na citrate/HCl, 1 to 500 mmol/l, of either glucosamine or fructose and a pH of 6.

19. The composition of claim 18, wherein said glycosamine or fructose is present at a concentration of from 10 to 300 mmol/l.

20. The composition of claim 1 having 50 mmol/l Na citrate/HCl 1 to 300 mmol/l of a nucleotide selected from the group consisting of thymidine, cytosine and uridine and a pH of 6.

21. The composition of claim 20, wherein said thymidine, cytosine or uridine is present at a concentration of from 10 to 300 mmol/l.

22. The composition of claim 1 having 50 mmol/l Na citrate, and 0.001 to 1 mol/1 of an acid selected from the group consisting of malic acid, lactic acid, fumaric acid and 2-oxoglutaric acid and a pH of 6.

23. The composition of claim 22, wherein said acid is present at a concentration of from 0.01 to 0.5 mol/1.

24. The composition of claim 1 having 50 mmol/1 Na citrate and a pH of 6.

25. The composition of claim 1, further comprising at least one pharmaceutically acceptable adjuvant, filler or carries material.

* * * * *